United States Patent [19]

Cantatore et al.

[11] Patent Number: 5,116,893
[45] Date of Patent: May 26, 1992

[54] PIPERIDYLAMINOTRIAZINE DERIVATIVES AND THEIR USE AS STABILIZERS

[75] Inventors: Giuseppe Cantatore, Bitonto; Valerio Borzatta; Franca Masina, both of Bologna, all of Italy

[73] Assignee: Ciba-Geigy Corporation, Ardsley, N.Y.

[21] Appl. No.: 638,609

[22] Filed: Jan. 7, 1991

Related U.S. Application Data

[60] Division of Ser. No. 453,061, Dec. 8, 1989, Pat. No. 4,997,938, which is a continuation of Ser. No. 192,974, May 12, 1988, abandoned.

[30] Foreign Application Priority Data

May 22, 1987 [IT]  Italy ............................... 20641 A/87

[51] Int. Cl.$^5$ .............................................. C08K 5/34
[52] U.S. Cl. .................................... 524/100; 524/98
[58] Field of Search ............................. 524/98, 100

[56] References Cited

U.S. PATENT DOCUMENTS 4,108,829  8/1978  Cassandrini et al. ............... 260/45.8

FOREIGN PATENT DOCUMENTS 70386    1/1983  European Pat. Off. .
112690   7/1984  European Pat. Off. .
176106   8/1987  European Pat. Off. .
57-38589 8/1982  Japan .

Primary Examiner—Johann Richter
Attorney, Agent, or Firm—JoAnn Villamizar

[57] ABSTRACT

The novel compounds of the formula (I)

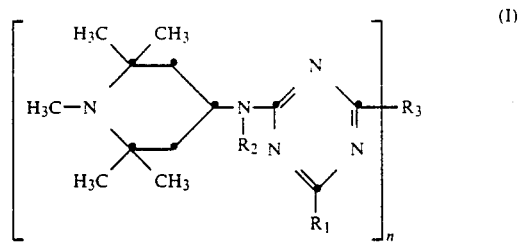

in which $R_1$ is di($C_1$-$C_4$-alkyl)amino, $C_1$-$C_4$-alkoxy, a 5-membered to 7-membered nitrogen containing heterocyclic group with the nitrogen atom bonded to the triazine ring, or a group of the formula (II),

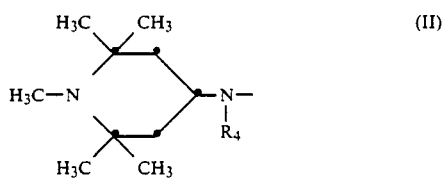

$R_2$ and $R_4$ which are identical or different are $C_1$-$C_{12}$-alkyl, $C_5$-$C_7$-cycloalkyl, benzyl or 1,2,2,6,6-pentamethyl-4-piperidyl, n is 2 or 3 and, if n is 2, $R_3$ is a group

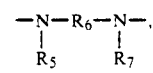

with $R_5$ and $R_7$, which are identical or different, being hydrogen, $C_1$-$C_{12}$-alkyl, $C_5$-$C_7$-cycloalkyl, benzyl or 1,2,2,6,6-pentamethyl-4-piperidyl and $R_6$ being $C_2$-$C_{12}$-alkylene, cyclohexylene, cyclohexylenedimethylene or methylenedicyclohexylene, or $R_3$ is the divalent radical or a 6-membered to 7-membered heterocyclic compound with two nitrogen atoms which are each bonded to a triazine ring, or, if n is 3, $R_3$ is a group

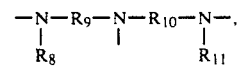

with $R_8$ and $R_{11}$, which are identical or different, being as defined above for $R_5$ and $R_7$, and $R_9$ and $R_{10}$, which are identical or different, being $C_2$-$C_{12}$-alkylene, are useful as light stabilizers, heat stabilizers and oxidation stabilizers for organic materials.

11 Claims, No Drawings

PIPERIDYLAMINOTRIAZINE DERIVATIVES AND THEIR USE AS STABILIZERS

This is a divisional of application Ser. No. 453,061 filed on Dec. 8, 1989 now U.S. Pat. No. 4,997,938 which is a continuation of Ser. No. 192,974 filed May 12, 1988, now abandoned.

The present invention relates to novel 1,2,2,6,6-pentamethyl-4-piperidylaminotriazine derivatives which can be used as light stabilizers, heat stabilizers and oxidation stabilizers for organic materials, especially synthetic polymers.

It is known that synthetic polymers undergo progressive changes in their physical properties, such as loss of mechanical strength and colour changes, when they are exposed to sunlight or other sources of ultraviolet light.

To retard the deleterious effect of ultraviolet radiation on synthetic polymers, it has been proposed to use various additives having light-stabilizing properties, such as certain benzophenone and benzotriazole derivatives, nickel complexes, alkylidenemalonates, cyanoacrylates and sterically hindered amines.

Japanese Patent Publication Sho 57-38589, EP-A-112 690 and EP-A-70386 describe polyalkylpiperidylaminotriazine derivatives and their use as light stabilizers, heat stabilizers and oxidation stabilizers for polymeric materials.

The present invention relates to compounds of the formula (I)

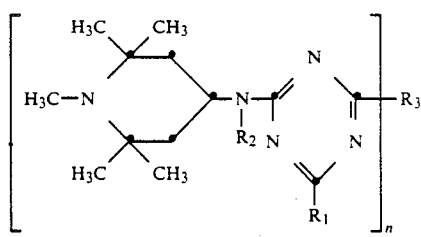

in which $R_1$ is di($C_1-C_4$-alkyl)amino, $C_1-C_4$-alkoxy, a 5-membered to 7-membered nitrogen containing heterocyclic group with the nitrogen atom bonded to the triazine ring, or a group of the formula (II),

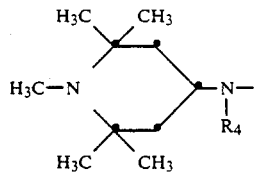

$R_2$ and $R_4$ which are identical or different are $C_1-C_{12}$-alkyl, $C_5-C_7$-cycloalkyl, benzyl or 1,2,2,6,6-pentamethyl-4-piperidyl, n is 2 or 3 and, if n is 2, $R_3$ is a group

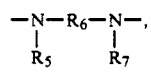

with $R_5$ and $R_7$, which are identical or different, being hydrogen, $C_1-C_{12}$-alkyl, $C_5-C_7$-cycloalkyl, benzyl or 1,2,2,6,6-pentamethyl-4-piperidyl and $R_6$ being $C_2-C_{12}$-alkylene, cyclohexylene, cyclohexylenedimethylene or methylenedicyclohexylene, or $R_3$ is the divalent radical of a 6-membered to 7-membered heterocyclic compound with two nitrogen atoms which are each bonded to a triazine ring, or, if n is 3, $R_3$ is a group

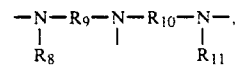

with $R_8$ and $R_{11}$, which are identical or different, being as defined above for $R_5$ and $R_7$, and $R_9$ and $R_{10}$, which are identical or different, being $C_2-C_{12}$-alkylene.

Representative examples of $R_1$ as di($C_1-C_4$-alkyl)amino are dimethylamino, diethylamino, dipropylamino, diisopropylamino, dibutylamino and diisobutylamino. Dimethylamino is preferred.

Representative examples of $R_1$ as $C_1-C_4$-alkoxy are methoxy, ethoxy, propoxy, isopropoxy, butoxy and isobutoxy.

Representative examples of $R_1$ as a 5-membered to 7-membered nitrogen containing heterocyclic group are 1-pyrrolidinyl, 1-piperidinyl, 4-morpholinyl and 1-hexahydroazepinyl. 4-morpholinyl is preferred.

Representative examples of $R_2$, $R_4$, $R_5$, $R_7$, $R_8$ and $R_{11}$ as $C_1-C_{12}$-alkyl are methyl, ethyl, propyl, isopropyl, butyl, 2-butyl, isobutyl, t-butyl, pentyl, hexyl, heptyl, octyl, 2-ethylhexyl, decyl, undecyl and dodecyl. $R_2$ and $R_4$ are preferably $C_1-C_8$-alkyl and $R_5$, $R_7$, $R_8$ and $R_{11}$ are preferably $C_1-C_4$-alkyl.

$R_2$, $R_4$, $R_5$, $R_7$, $R_8$ and $R_{11}$ as $C_5-C_7$-cycloalkyl are for example cyclopentyl, cyclohexyl or cycloheptyl. Cyclohexyl is preferred.

Representative examples of $R_6$, $R_9$ and $R_{10}$ as $C_2-C_{12}$-alkylene are ethylene, propylene, trimethylene, tetramethylene, pentamethylene, 2,2-dimethyltrimethylene, hexamethylene, trimethylhexamethylene, decamethylene and dodecamethylene. $C_2-C_6$-alkylene is preferred.

Representative examples of $R_3$ as a radical of a 6-membered to 7-membered heterocyclic compound with two nitrogen atoms are:

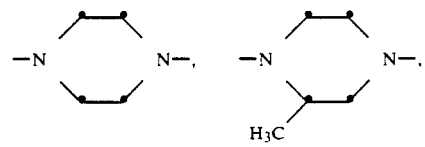

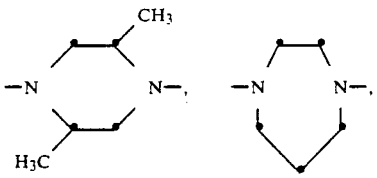

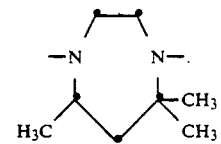

1,4-Piperazinediyl is preferred.

Those compounds of the formula (I) are preferred, in which $R_1$ is di-($C_1-C_3$-alkyl)amino, 4-morpholinyl or a group of the formula (II), $R_2$ and $R_4$ which are identical or different are $C_1-C_8$-alkyl, cyclohexyl or 1,2,2,6,6-pentamethyl-4-piperidyl, n is 2 or 3 and, if n is 2, $R_3$ is a group

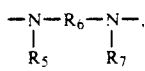

with $R_5$ and $R_7$, which are identical or different, being hydrogen, $C_1$–$C_4$-alkyl or 1,2,2,6,6-pentamethyl-4-piperidyl and $R_6$ being $C_2$–$C_6$-alkylene, cyclohexylenedimethylene or methylenedicyclohexylene, or $R_3$ is 1,4-piperazinediyl or 5,5,7-trimethyl-1,4-homopiperazinediyl, or, if n is 3, $R_3$ is a group

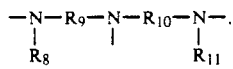

with $R_8$ and $R_{11}$, which are identical or different, being hydrogen, $C_1$–$C_4$-alkyl or 1,2,2,6,6-pentamethyl-4-piperidyl and $R_9$ and $R_{10}$, which are identical or different, being $C_2$–$C_6$-alkylene.

Those compounds of the formula (I) are also preferred, in which $R_1$ is 4-morpholinyl or a group of the formula (II), $R_2$ and $R_4$ which are identical or different are $C_1$–$C_8$-alkyl or 1,2,2,6,6-pentamethyl-4-piperidyl, n is 2 or 3 and, if n is 2, $R_3$ is a group

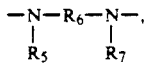

with $R_5$ and $R_7$, which are identical or different, being hydrogen, $C_1$–$C_4$-alkyl or 1,2,2,6,6-pentamethyl-4-piperidyl and $R_6$ being $C_2$–$C_6$-alkylene or cyclohexylenedimethylene, or $R_3$ is 1,4-piperazinediyl, or, if n is 3, $R_3$ is a group

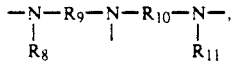

with $R_8$ and $R_{11}$, which are identical or different, being hydrogen, $C_1$–$C_4$-alkyl or 1,2,2,6,6-pentamethyl-4-piperidyl and $R_9$ and $R_{10}$, which are identical or different, being $C_2$–$C_6$-alkylene.

Compounds of the formula (I) of particular interest are those, in which $R_1$ is a group of the formula (II), $R_2$ and $R_4$ which are identical or different are $C_1$–$C_8$-alkyl or 1,2,2,6,6-pentamethyl-4-piperidyl, n is 2 or 3, $R_5$, $R_7$, $R_8$ and $R_{11}$ which are identical or different are hydrogen, $C_1$–$C_4$-alkyl or 1,2,2,6,6-pentamethyl-4-piperidyl and $R_6$, $R_9$ and $R_{10}$ which are identical or different are $C_2$–$C_6$-alkylene.

Compounds of the formula (I) of special interest are those, in which $R_1$ is a group of the formula (II), $R_2$ and $R_4$ which are identical or different are $C_1$–$C_4$-alkyl, n is 2 or 3, $R_5$, $R_7$, $R_8$ and $R_{11}$ which are identical or different are hydrogen, methyl or 1,2,2,6,6-pentamethyl-4-piperidyl, $R_6$, $R_9$ and $R_{10}$ which are identical or different are $C_2$–$C_6$-alkylene.

Preferred examples of compounds of the formula (I) are:

N,N′-bis-[1,2,2,6,6-pentamethyl-4-piperidyl]-N,N′-bis-[2,4-bis-[N″-(1,2,2,6,6-pentamethyl-4-piperidyl)-methylamino]-1,3,5-triazin-6-yl]-1,6-hexanediamine,
N,N′-bis-[1,2,2,6,6-pentamethyl-4-piperidyl]-N,N′-bis-[2,4-bis-[N″-(1,2,2,6,6-pentamethyl-4-piperidyl)-ethylamino]-1,3,5-triazin-6-yl]-1,6-hexanediamine,
1,4,7-tris-[2,4-bis-[N-(1,2,2,6,6-pentamethyl-4-piperidyl)-methylamino]-1,3,5-triazin-6-yl]-1,7-dimethyl-1,4,7-triazaheptane,
1,5,9-tris-[2,4-bis-[N-(1,2,2,6,6-pentamethyl-4-piperidyl)-methylamino]-1,3,5-triazin-6-yl]-1,9-dimethyl-1,5,9-triazanonane,
1,4,7-tris-[2,4-bis-[N-(1,2,2,6,6-pentamethyl-4-piperidyl)-ethylamino]-1,3,5-triazin-6-yl]-1,7-dimethyl-1,4,7-triazaheptane.

The compounds of the formula (I) can be prepared by N-methylation of the compounds of the formula (III)

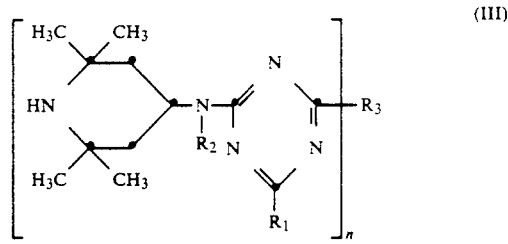

in which $R_1$, $R_2$, $R_3$ and n are as defined above, by means of any of the known N-methylation processes, for example by reacting the compounds of the formula (III) with formaldehyde and formic acid. The molar ratio of the >NH groups in the compounds of the formula (III), formaldehyde and formic acid is conveniently 1:1:1 to 1:3:4.

This process is known as the Eschweiler-Clarke reaction and preferably carried out at a temperature of 50° to 100° C., in particular at a temperature of 80° to 100° C., in water.

The compounds of the formula (I) can also be prepared by reacting a compound of the formula (III) with formaldehyde (molar ratio of the >NH groups and formaldehyde e.g. 1:1 to 1:3) and hydrogen in the presence of a hydrogenation catalyst, e.g. platinum or palladium.

This reaction is preferably carried out in an organic solvent, e.g. toluene, xylene, 1,3,5-trimethylbenzene or decaline, at a temperature of 80° to 180° C., preferably 100° to 150° C., and a hydrogen pressure of 5 to 100 bar, preferably 10 to 50 bar.

In the methylation of compounds of the formula (III), especially when the Eschweiler-Clarke reaction is used, a total or partial methylation of the groups >NH bonded to the triazine rings is possible in addition to the methylation of the piperidine >NH groups.

The compounds of the formula (III) can be prepared by known processes, for example as described in U.S. Pat. No. 4,108,829.

The compounds of the formula (I) are very effective in improving the light stability, heat stability and oxidation stability of organic materials, especially synthetic polymers, e.g. polyolefins. In particular, the remarkable antioxidant action, especially in polyolefins, in addition to the light stabilizing efficiency is surprising.

In general polymers which can be stabilized include:
1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE/EVA, LDPE/EAA, LLDPE/EVA and LLDPE/EAA.

3a. Hydrocarbon resins (for example C$_5$-C$_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylenediamine and adipic acid; polyamides prepared from hexamethylenediamine and isophthalic or/and terephthalic acid and optionally an elastomer as modifier, for example poly-2,4,4-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2,-(4-hydroxyphenyl)-propane] terephthalate and polyhydroxybenzoates as well as block-copolyetheresters derived from polyethers having hydroxyl end groups.

18. Polycarbonates and polyester-carbonates.

19. Polysulfones, polyether-sulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trime]lithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

Therefore, a further object of the present invention is a composition comprising an organic material subject to thermal, oxidative or light-induced degradation and at least one compound of the formula (I).

The compounds of the formula (I) are especially useful as stabilizers for those organic materials mentioned above under items 1, 2 and 3. Of particular technical interest are polyethylene and polypropylene.

The compounds of the formula (I) can be added to the organic material in various proportions depending on the nature of the material to be stabilized, the end use and the presence of other additives. In general, it is appropriate to use 0.01 to 5% by weight of the compounds of the formula (I), relative to the weight of the polymers, preferably from 0.05 to 1%.

The compounds of the formula (I) can be incorporated into the polymeric materials by various processes, such as dry blending in the form of powders or granules, or wet mixing in the form of solutions or suspensions or also in the form of a master-batch.

The polymers stabilized with the products of the formula (I) can be used for the preparation of moulded articles, films, tapes, monofilaments and the like.

If desired, other additives, sucha s antioxidants, UV absorbers, nickel stabilizers, pigments, fillers, plasticizers, antistatic agents, flame-proofing agents, lubricants, corrosion inhibitors and metal deactivators, can be added to the mixtures of the compounds of the formula (I) with the organic materials. Examples of additives which can be mixed with the compounds of the formula (I) are in particular:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis-(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis-(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl] terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example lauric acid 4-hydroxyanilide, stearic acid 4-hydroxyanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylene-diamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The following examples illustrate the present invention.

EXAMPLE 1

47.37 g (0.05 mol) of N,N'-bis-[2,4-bis-[N''-(2,2,6,6-tetramethyl-4-piperidyl)-methylamino]-1,3,5-triazin-6-yl]-1,6-hexanediamine are dissolved at ambient temperature in a solution of 27.62 g (0.6 mol) of formic acid in 70 ml of water. 18 g (0.6 mol) of paraformaldehyde are added to the solution which is then heated under reflux for 10 hours. After cooling to ambient temperature, a solution of 32 g of sodium hydroxide in 200 ml of water is added; the precipitate obtained is separated off by filtration, washed thoroughly and dried at 100° C. in vacuo (2 mbar). This gives the product of the formula

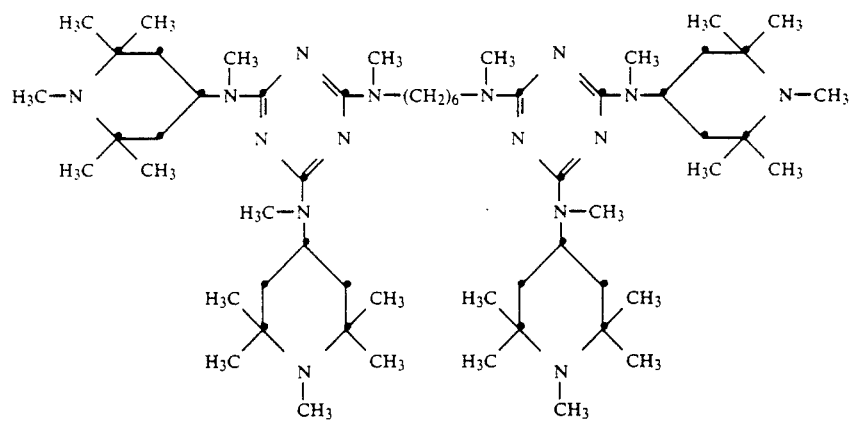

of melting point 141°-142° C.

Analysis for $C_{58}H_{110}N_{16}$: Calculated: C=67.53%; H=10.75%; N=21.72%. Found: C=67.53%; H=10.71%; N=21.71%.

EXAMPLES 2-25

Following the procedure described in Example 1 and using the appropriate intermediates, the following compounds of the formula

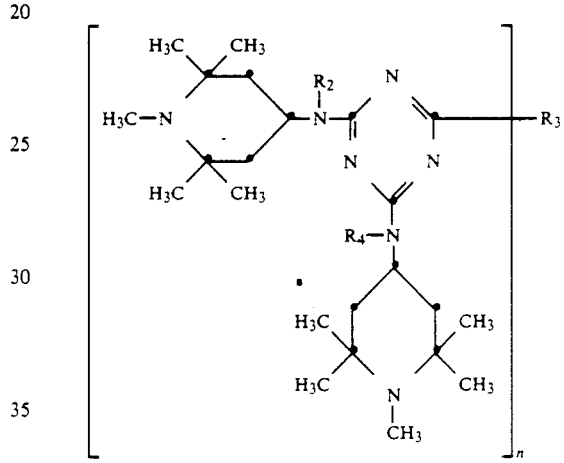

are prepared.

| Ex. | n | $R_2/R_4$ | $R_3$ | m.p. (°C.) |
|---|---|---|---|---|
| 2 | 2 | —CH$_3$ | ![structure with —N—(CH$_2$)$_6$—N— and two tetramethylpiperidine N-CH$_3$ groups] | 262-265 |
| 3 | 2 | —C$_2$H$_5$ | —N—(CH$_2$)$_6$—N—<br>   |              |<br>  CH$_3$          CH$_3$ | 142-144 |
| 4 | 2 | —C$_2$H$_5$ | ![structure with —N—(CH$_2$)$_6$—N— and two tetramethylpiperidine N-CH$_3$ groups] | 207-210 |
| 5 | 2 | —C$_2$H$_5$ | —N—(CH$_2$)$_6$—N—<br>   |              |<br>  C$_3$H$_7$(i)   C$_3$H$_7$(i) | 256-258 |

-continued
| Ex. | n | R$_2$/R$_4$ | R$_3$ | m.p. (°C.) |
|---|---|---|---|---|
| 6 | 2 | —C$_2$H$_5$ | —N(CH$_3$)—(CH$_2$)$_3$—N(CH$_3$)— | 155–158 |
| 7 | 2 | —C$_4$H$_9$(n) | —N(CH$_3$)—(CH$_2$)$_6$—N(CH$_3$)— | 116–118 |
| 8 | 2 | —C$_4$H$_9$(n) | 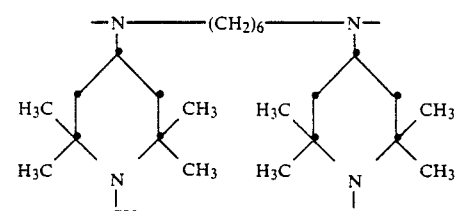 | 231–232 |
| 9 | 2 | —C$_4$H$_9$(n) | 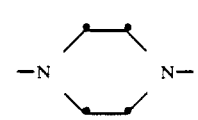 | 240–243 |
| 10 | 2 | —C$_4$H$_9$(n) | —N(C$_3$H$_7$(i))—(CH$_2$)$_6$—N(C$_3$H$_7$(i))— | 131–133 |
| 11 | 2 | —C$_4$H$_9$(sec) | —N(CH$_3$)—(CH$_2$)$_6$—N(CH$_3$)— | 188–191 |
| 12 | 2 | —C$_4$H$_9$(sec) | 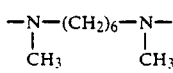 | 275–278 |
| 13 | 2 | —C$_3$H$_7$(iso) | —N(CH$_3$)—(CH$_2$)$_6$—N(CH$_3$)— | 167–172 |
| 14 | 2 | —C$_3$H$_7$(iso) | 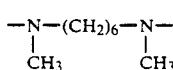 | 205–208 |
| 15 | 2 | —C$_8$H$_{17}$(n) | 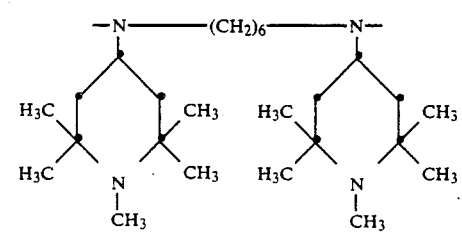 | 109–112 |

-continued

| Ex. | n | R$_2$/R$_4$ | R$_3$ | m.p. (°C.) |
|---|---|---|---|---|
| 16 | 2 | —CH$_2$CH(C$_2$H$_5$)—C$_4$H$_9$ | —N[2,2,6,6-tetramethyl-1-methyl-4-piperidyl]—(CH$_2$)$_6$—N[2,2,6,6-tetramethyl-1-methyl-4-piperidyl]— | 111–115 |
| 17 | 2 | 2,2,6,6-tetramethyl-1-methyl-4-piperidyl | —N(CH$_3$)—(CH$_2$)$_6$—N(CH$_3$)— | 219–222 |
| 18 | 2 | 2,2,6,6-tetramethyl-1-methyl-4-piperidyl | —N(C$_3$H$_7$(i))—(CH$_2$)$_6$—N(C$_3$H$_7$(i))— | 300–306 |
| 19 | 2 | 2,2,6,6-tetramethyl-1-methyl-4-piperidyl | —N(CH$_3$)—CH$_2$—(cyclohexyl)—CH$_2$—N(CH$_3$)— | 247–251 |
| 20 | 3 | —CH$_3$ | —N(CH$_3$)—(CH$_2$)$_2$—N—(CH$_2$)$_2$—N(CH$_3$)— | 194–196 |
| 21 | 3 | —CH$_3$ | —N(CH$_3$)—(CH$_2$)$_3$—N—(CH$_2$)$_3$—N(CH$_3$)— | 179–182 |
| 22 | 3 | —C$_2$H$_5$ | —N(CH$_3$)—(CH$_2$)$_2$—N—(CH$_2$)$_2$—N(CH$_3$)— | 186–190 |
| 23 | 3 | —C$_2$H$_5$ | —N(CH$_3$)—(CH$_2$)$_3$—N—(CH$_2$)$_3$—N(CH$_3$)— | 166–168 |
| 24 | 3 | —C$_4$H$_9$(n) | —N(CH$_3$)—(CH$_2$)$_2$—N—(CH$_2$)$_2$—N(CH$_3$)— | 145–150 |
| 25 | 3 | —C$_4$H$_9$(n) | —N(CH$_3$)—(CH$_2$)$_3$—N—(CH$_2$)$_3$—N(CH$_3$)— | 143–147 |
| 26 | 3 | —C$_2$H$_5$ | —N(CH$_3$)—(CH$_2$)$_6$—N—(CH$_2$)$_6$—N(CH$_3$)— | 149–154 |

EXAMPLE 27

50.17 g (0.05 mol) of N,N'-bis-[2,4-bis-[N''-(2,2,6,6-tetramethyl-4-piperidyl)-ethylamino]-1,3,5-triazin-6-yl]-1,6-hexanediamine, 400 ml of xylene, 18 g (0.6 mol) of paraformaldehyde and 6 g of 10% Pd on carbon are introduced into a 1 liter autoclave. After flushing with nitrogen, hydrogenation is carried out at 130°–140° C. under a pressure of 40 bar. After the absorption of hydrogen has ceased, the reaction mixture is cooled to ambient temperature, the catalyst is filtered off, and the filtrate is evaporated in vacuo. This gives a product of the formula

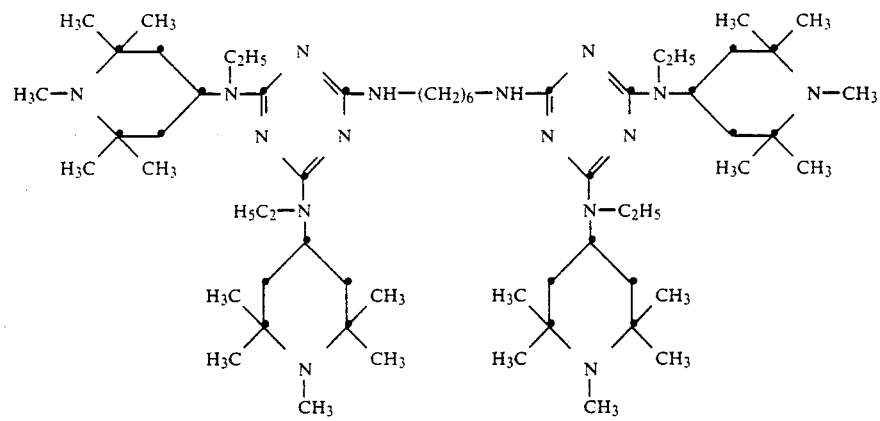

of melting point 118°–121° C.

Analysis for $C_{60}H_{114}N_{16}$: Calculated: $C=68.01\%$; $H=10.84\%$; $N=21.15\%$. Found: $C=67.77\%$; $H=10.81\%$; $N=20.98\%$.

EXAMPLES 28–34

Following the procedure described in Example 27 and using the appropriate intermediates, the following compounds of the formula

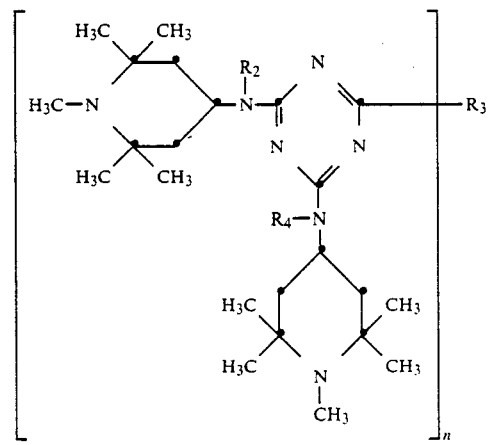

are prepared.

| Ex. | n | $R_2/R_4$ | $R_3$ | m.p. (°C.) |
|---|---|---|---|---|
| 28 | 2 | $-C_4H_9(n)$ | $-NH-(CH_2)_6-NH-$ | 108–113 |
| 29 | 2 | 2,2,6,6-tetramethyl-N-methylpiperidin-4-yl | $-N-(CH_2)_3-NH-$ attached to piperidine ring | 266–270 |
| 30 | 2 | 2,2,6,6-tetramethyl-N-methylpiperidin-4-yl | $-N-(CH_2)_3-NH-$ with $C_8H_{17}(n)$ | 194–198 |
| 31 | 3 | $-C_2H_5$ | $-NH-(CH_2)_2-N-(CH_2)_2-NH-$ | 219–221 |
| 32 | 3 | $-C_2H_5$ | $-NH-(CH_2)_3-N-(CH_2)_3-NH-$ | 185–187 |
| 33 | 3 | $-CH_3$ | $-NH-(CH_2)_2-N-(CH_2)_2-NH-$ | 227–231 |

-continued

| Ex. | n | R₂/R₄ | R₃ | m.p. (°C.) |
|---|---|---|---|---|
| 34 | 2 | H₃C, CH₃ ring with N—CH₃/—C₄H₉(n), H₃C, CH₃ | —NH—(CH₂)₆—NH— | 146–149° C. |

EXAMPLES 35–36

Following the procedure described in Example 1 and using the appropriate intermediates, the following compounds of the formula

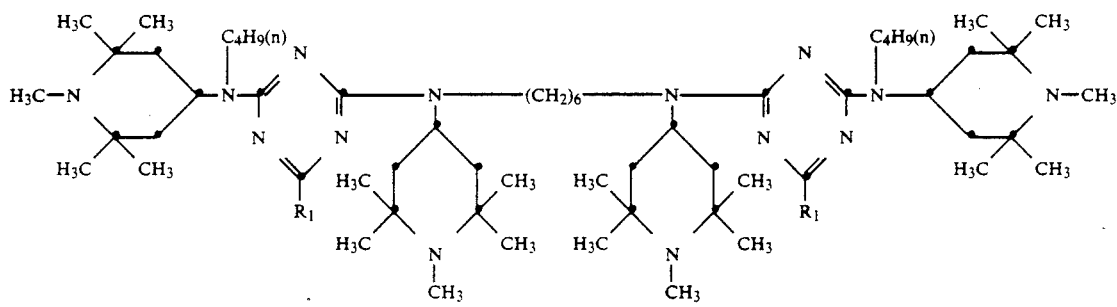

are prepared.

| Example | R₁ | m.p. (°C.) |
|---|---|---|
| 35 | —N(morpholino ring with O) | 224–226 |
| 36 | —N(CH₃)₂ | 131–135 |

EXAMPLE 37

Antioxidant action in polypropylene plaques 1 g of each of the compounds indicated in Table 1 and 1 g of calcium stearate are mixed in a slow mixer with 1,000 g of polypropylene powder of melt index=2 g/10 minutes (measured at 230° C. and 2.16 kg).

The mixtures are extruded twice at 200°–220° C. to give polymer granules which are then converted into plaques of 1 mm thickness (mould according to DIN 53,451) by compression moulding for 3 minutes at 220° C. The plaques obtained are exposed in a forced-circulation air oven maintained at a temperature of 135° C. and are periodically checked by bending through 180°, in order to determine the time (in hours) required for the onset of embrittlement.

The results obtained are shown in Table 1.

TABLE 1

| Stabilizer | Time to embrittlement (hours) |
|---|---|
| Without stabilizer | 250 |
| Compound of Example 1 | 1500 |
| Compound of Example 2 | 1780 |
| Compound of Example 3 | 1500 |
| Compound of Example 4 | 1260 |
| Compound of Example 5 | 1520 |
| Compound of Example 6 | 1610 |
| Compound of Example 7 | 1180 |
| Compound of Example 17 | 1100 |
| Compound of Example 19 | 1540 |
| Compound of Example 20 | 1610 |
| Compound of Example 21 | 1820 |
| Compound of Example 22 | 1580 |
| Compound of Example 25 | 1320 |
| Compound of Example 31 | 1500 |
| Compound of Example 35 | 1370 |

EXAMPLE 38

Light stabilizing action in polypropylene tapes 1 g of each of the compounds indicated in Table 2, 0.5 g of tris-(2,4-di-t-butylphenyl)phosphite, 0.5 g of pentaerythritol tetrakis-[3-(3,5-di-t-butyl-4-hydroxyphenyl)-propionate] and 1 g of calcium stearate are mixed in a slow mixer with 1000 g of polypropylene powder of melt index=2 g/10 minutes (measured at 230° C. and 2.16 kg). The mixtures are extruded at 200°–220° C. to give polymer granules which are then converted into stretched tapes of 50 μm thickness and 2.5 mm width, using a pilot type apparatus (Leonard-Sumirago (VA) Italy) under the following conditions:
extruder temperature=210°–230° C.
head temperature=240°–260° C.
stretch ratio=1:6

The tapes thus prepared are exposed, mounted on a white card, in a model 65 WR weather-O-meter (ASTM G 26-77), with a black panel temperature of 63° C. The residual tenacity is measured on samples, taken after various times of exposure to light, by means of a constant-speed tensometer; the exposure time (in hours) needed to halve the initial tenacity is then calculated ($T_{50}$).

The results obtained are shown in Table 2.

TABLE 2

| Stabilizer | $T_{50}$ (hours) |
|---|---|
| Without stabilizer | 400 |

TABLE 2-continued

| Stabilizer | $T_{50}$ (hours) |
|---|---|
| Compound of Example 1 | 1920 |
| Compound of Example 2 | 1850 |
| Compound of Example 3 | 1750 |
| Compound of Example 4 | 1880 |
| Compound of Example 6 | 1950 |
| Compound of Example 7 | 1900 |
| Compound of Example 8 | 1670 |
| Compound of Example 9 | 1710 |
| Compound of Example 15 | 1780 |
| Compound of Example 16 | 1730 |
| Compound of Example 22 | 1850 |
| Compound of Example 24 | 1620 |

What is claimed is:

1. A composition comprising an organic material subject to thermal, oxidative or light-induced degradation and an effective stabilizing amount of a compound of the formula (I)

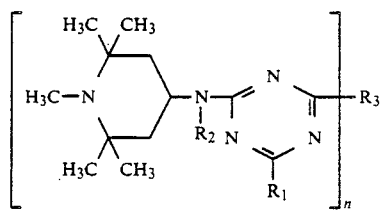

in which $R_1$ is di($C_1$–$C_4$-alkyl)amino, $C_1$–$C_4$-alkoxy, a 5-membered to 7-membered nitrogen containing heterocyclic group with the nitrogen atom bonded to the triazine ring, or a group of the formula (II),

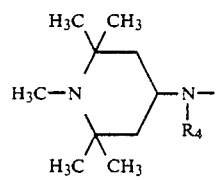

$R_2$ and $R_4$ which are identical or different are $C_1$–$C_{12}$-alkyl, $C_5$–$C_7$-cycloalkyl, benzyl or 1,2,2,6,6-pentamethyl-4-piperidyl, n is 2 or 3 and, if n is 2, $R_3$ is a group

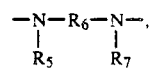

with $R_5$ and $R_7$, which are identical or different, being hydrogen, $C_1$–$C_{12}$-alkyl, $C_5$–$C_7$-cycloalkyl, benzyl or 1,2,2,6,6-pentamethyl-4-piperidyl and $R_6$ being $C_2$–$C_{12}$-alkylene, cyclohexylene, cyclohexylenedimethylene or methylenedicyclohexylene, or $R_3$ is the divalent radical of a 6-membered to 7-membered heterocyclic compound with two nitrogen atoms which are each bonded to a triazine ring, or, if n is 3, $R_3$ is a group

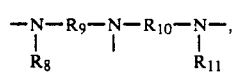

with $R_8$ and $R_{11}$, which are identical or different, being as defined above for $R_5$ and $R_7$, and $R_9$ and $R_{10}$, which are identical or different, being $C_2$–$C_{12}$-alkylene.

2. A composition according to claim 1, wherein the organic material is a synthetic polymer.

3. A composition according to claim 2, which, in addition to the compound of the formula (I), also comprises other conventional additives for synthetic polymers.

4. A composition according to claim 1, wherein the organic material is a polyolefine.

5. A composition according to claim 1, wherein the organic material is polyethylene or polypropylene.

6. A composition according to claim 1 wherein $R_1$ is di($C_1$–$C_3$-alkyl)amino, 4-morpholinyl or a group of the formula (II), $R_2$ and $R_4$ which are identical or different are $C_1$–$C_8$alkyl, cyclohexyl or 1,2,2,6,6-pentamethyl-4-piperidyl, n is 2 or 3 and, if n is 2, $R_3$ is a group

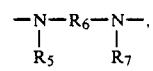

with $R_5$ and $R_7$, which are identical or different, being hydrogen, $C_1$–$C_4$-alkyl or 1,2,2,6,6-pentamethyl-4-piperidyl and $R_6$ being $C_2$–$C_6$-alkylene, cyclohexylenedimethylene or methylenedicyclohexylene, or $R_3$ is 1,4-piperazinediyl or 5,5,7-trimethyl-1,4-homopiperazinediyl, or, if n is 3, $R_3$ is a group

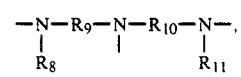

with $R_8$ and $R_{11}$, which are identical or different, being hydrogen, $C_1$–$C_4$-alkyl or 1,2,2,6,6-pentamethyl-4-piperidyl and $R_9$ and $R_{10}$, which are identical or different, being $C_2$–$C_6$-alkylene.

7. A composition according to claim 1 wherein $R_1$ is 4-morpholinyl or a group of the formula (II), $R_2$ and $R_4$ which are identical or different are $C_1$–$C_8$-alkyl or 1,2,2,6,6-pentamethyl-4-piperidyl, n is 2 or 3 and, if n is 2, $R_3$ is a group

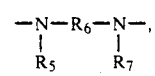

with $R_5$ and $R_7$, which are identical or different, being hydrogen, $C_1$–$C_4$-alkyl or 1,2,2,6,6-pentamethyl-4-piperidyl and $R_6$ being $C_2$–$C_6$-alkylene or cyclohexylenedimethylene, or $R_3$ is 1,4-piperazinediyl, or, if n is 3, $R_3$ is a group

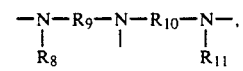

with $R_8$ and $R_{11}$, which are identical or different, being hydrogen, $C_1$–$C_4$-alkyl or 1,2,2,6,6-pentamethyl-4-piperidyl and $R_9$ and $R_{10}$, which are identical or different, being $C_2$–$C_6$-alkylene.

8. A composition according to claim 1 wherein $R_1$ is a group of the formula (II), $R_2$ and $R_4$ which are identical or different are $C_1$–$C_8$-alkyl or 1,2,2,6,6-pentamethyl-4-piperidyl, n is 2 or 3, $R_5$, $R_7$, $R_8$ and $R_{11}$ which are identical or different are hydrogen, $C_1$–$C_4$-alkyl or 1,2,2,6,6-pentamethyl-4-piperidyl and $R_6$, $R_9$ and $R_{10}$ which are identical or different are $C_2$–$C_6$-alkylene.

9. A composition according to claim 1 wherein $R_1$ is a group of the formula (II), $R_2$ and $R_4$ which are identical or different are $C_1$–$C_4$alkyl, n is 2 or 3, $R_5$, $R_7$, $R_8$ and $R_{11}$ which are identical or different are hydrogen, methyl or 1,2,2,6,6-pentamethyl-4-piperidyl, $R_6$, $R_9$ and $R_{10}$ which are identical or different are $C_2$–$C_6$-alkylene.

10. A composition according to claim 1 wherein said compound of formula I is selected from the group consisting of N,N'-bis-[1,2,2,6,6-pentamethyl-4-piperidyl]-N,N'-bis-[2,4-bis-[N''-(1,2,2,6,6-pentamethyl-4-piperidyl)-methylamino]-1,3,5-triazin-6-yl]-1,6-hexanediamine, N,N'-bis-[1,2,2,6,6-pentamethyl-4-piperidyl]-N,N'-bis-[2,4-bis-[N''-(1,2,2,6,6-pentamethyl-4-piperidyl)-ethylamino]-1,3,5-triazin-6-yl]-1,6-hexanediamine, 1,4,7-tris-[2,4-bis-[N-(1,2,2,6,6-pentamethyl-4-piperidyl)-methylamino]-1,3,5-triazin-6-yl]-1,7-dimethyl-1,4,7-triazaheptane, 1,5,9-tris-[2,4-bis-[N-(1,2,2,6,6-pentamethyl-4-piperidyl)-methylamino]-1,3,5-triazin-6-yl]-1,9-dimethyl-1,5,9-triazanonane, and 1,4,7-tris-[2,4-bis-[N-(1,2,2,6,6-pentamethyl-4-piperidyl)-ethylamino]-1,3,5-triazin-6-yl]-1,7-dimethyl-1,4,7-triazaheptane.

11. A method for stabilizing an organic material against thermal, oxidative or light-induced degradation, which comprises incorporating into the organic material an effective amount of a compound of the formula (I)

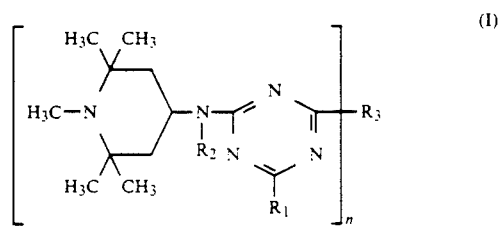

in which $R_1$ is di($C_1$–$C_4$-alkyl)amino, $C_1$–$C_4$-alkoxy, a 5-membered to 7-membered nitrogen containing heterocyclic group with the nitrogen atom bonded to the triazine ring, or a group of the formula (II),

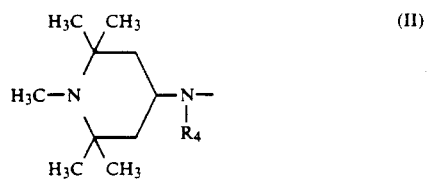

$R_2$ and $R_4$ which are identical or different are $C_1$–$C_{12}$-alkyl, $C_5$–$C_7$-cycloalkyl, benzyl or 1,2,2,6,6-pentamethyl-4-piperidyl, n is 2 or 3 and, if n is 2, $R_3$ is a group

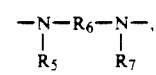

with $R_5$ and $R_7$, which are identical or different, being hydrogen, $C_1$–$C_{12}$-alkyl, $C_5$–$C_7$-cycloalkyl, benzyl or 1,2,2,6,6-pentamethyl-4-piperidyl and $R_6$ being $C_2$–$C_{12}$-alkylene, cyclohexylene, cyclohexylenedimethylene or methylenedicyclohexylene, or $R_3$ is the divalent radical of a 6-membered to 7-membered heterocyclic compound with two nitrogen atoms which are each bonded to a triazine ring, or, if n is 3, $R_3$ is a group

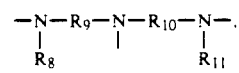

with $R_8$ and $R_{11}$, which are identical or different, being as defined above for $R_5$ and $R_7$, and $R_9$ and $R_{10}$, which are identical or different, being $C_2$–$C_{12}$-alkylene.

* * * * *